United States Patent [19]

Mizutani et al.

[11] Patent Number: 5,683,563
[45] Date of Patent: Nov. 4, 1997

[54] ENZYME ELECTRODE AND METHOD OF MANUFACTURING THE SAME

[75] Inventors: Fumio Mizutani, Tsuchiura; Yoshiki Hirata, Tokyo; Soichi Yabuki, Tsukuba, all of Japan

[73] Assignee: Director-General of Agency of Industrial Science and Technology, Tokyo, Japan

[21] Appl. No.: 579,629

[22] Filed: Dec. 26, 1995

[30] Foreign Application Priority Data

Dec. 26, 1994 [JP] Japan .................. 6-322585

[51] Int. Cl.$^6$ .................................. G01N 27/26
[52] U.S. Cl. .............. 204/403; 204/415; 435/287.1; 435/289.1; 435/817
[58] Field of Search .................. 204/403, 415, 204/418; 435/288, 291, 817, 289.1, 287.1

[56] References Cited

U.S. PATENT DOCUMENTS 4,525,457  6/1985  Sakata et al. .................. 435/178

FOREIGN PATENT DOCUMENTS

| 12437 | 1/1980 | Japan . |
| 274682 | 12/1986 | Japan . |
| 372254 | 3/1991 | Japan . |
| 491142 | 3/1992 | Japan . |

OTHER PUBLICATIONS

Mizutani et al.; "Amperometric–L–lactate–sensing electrode based on a polyion complex layer containing lactate oxidase. Application to serum and milk samples", *Analytica Chimica Acta* 314 (1995) pp. 233–239 no month available.

Mizutani et al.; "Amperometric Biosensors Using Poly–L–Lysine/Poly(styrenesulfonate) Membranes with Immobilized Enzymes", Denki Kagaku, 63, No. 12 (1995) no month available.

*Primary Examiner*—Bruce F. Bell

[57] ABSTRACT

There is disclosed an enzyme electrode, comprising a polyion complex membrane of an immobilized enzyme, formed on an electrode base. According to the enzyme electrode, an enzyme substrate or the like can be quantitatively determined with less hindrance of easily oxidizable coexistent materials, conveniently, exactly, and rapidly.

8 Claims, 1 Drawing Sheet

F I G. 1
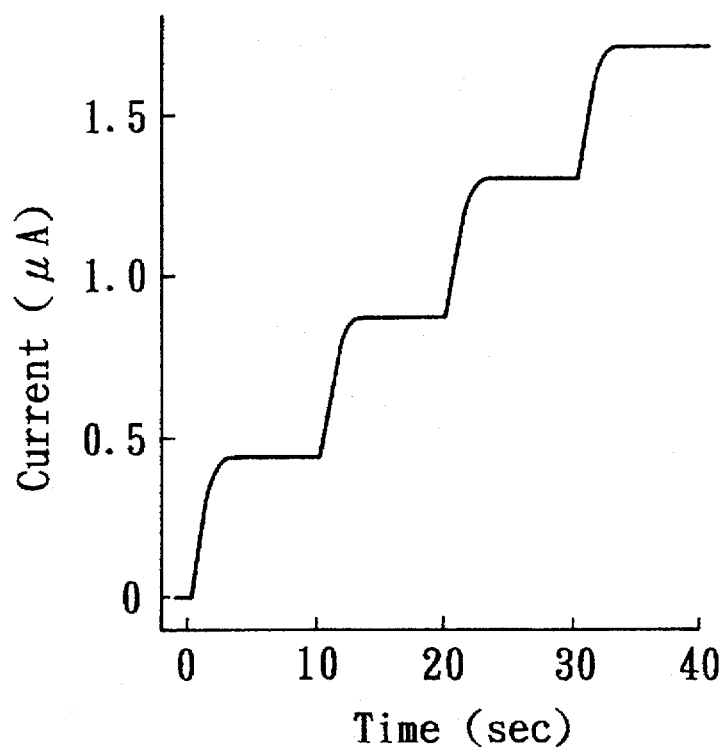
F I G. 2
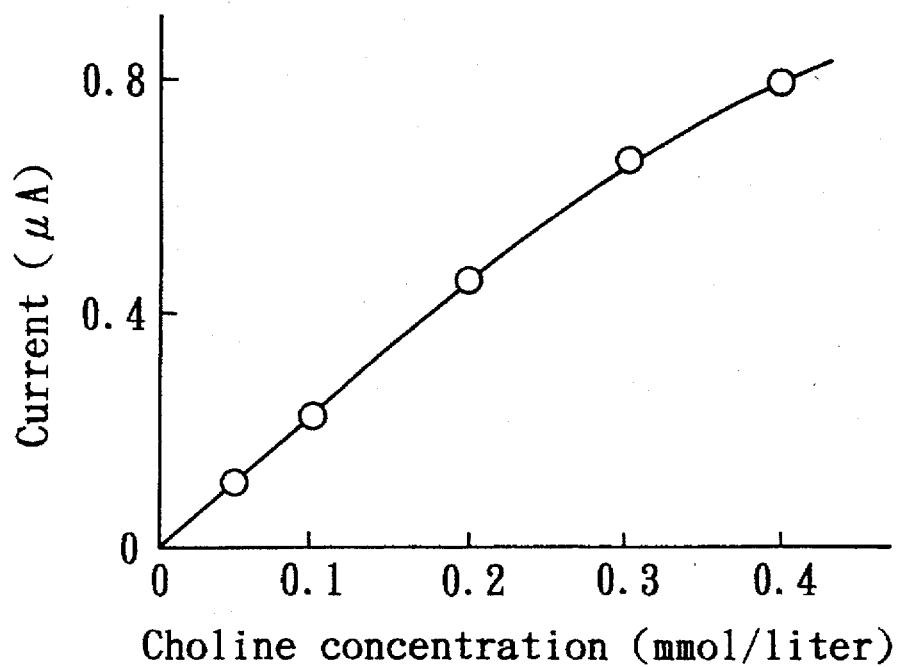

ENZYME ELECTRODE AND METHOD OF MANUFACTURING THE SAME

FIELD OF THE INVENTION

The present invention relates to an enzyme electrode; more particularly it relates to an enzyme electrode for quantitatively determining an enzyme substrate or the like conveniently, correctly, and rapidly. The present invention also relates to a production process of the enzyme electrode.

BACKGROUND OF THE INVENTION

An enzyme electrode comprises, in most cases, at least two membranes: an enzyme-immobilizing membrane (Membrane I, surface layer), and a selective permeation (permselective) membrane for electrode-active substance (Membrane II, lower layer), which membranes are disposed on an electrode as a base. When a sample is added to a solution in which the enzyme electrode is inserted, the substrate or the like in the sample reaches the Membrane I on the surface of the electrode. Then, an enzymatic reaction proceeds in the Membrane I, along which reaction an electrode-active substance is formed or consumed. The electrode-active substance permeates the Membrane II and gives an electrode current, and the electrode current also changes depending on the amount of the electrode-active substance formed or consumed. In a method of measuring the substrate or the like by the enzyme electrode, the concentration of the substrate in the sample is determined by the change of the electrode current with reference to a previously formed calibration curve.

For example, in an enzyme electrode for measuring the concentration of lactic acid in blood, a lactate oxidase-immobilizing membrane is disposed on an electrode for detecting hydrogen peroxide. Thereby the lactic acid concentration can be measured by a current value (flow of electron ($e^-$)) due to oxidation of hydrogen peroxide on the electrodes; that is,

$H_2O_2$ (hydrogen peroxide) → $2H^+ + O_2 + 2e^-$, which hydrogen peroxide is formed by an enzymatic reaction in the immobilizing membrane: lactic acid+enzyme→pyruvic acid+hydrogen peroxide.

The Membrane I is prepared by immobilizing an enzyme by a chemical bonding method, an entrapping method, or the like, which usually requires complicated procedures.

The Membrane II is used, for example, in an electrode for measurement of lactic acid based on the above-mentioned principle, to eliminate easily oxidizable ingredients, such as ascorbic acid, uric acid, and acetaminophene, contained in the blood. Since the ingredients are oxidized at a potential of causing electrolytic oxidation of hydrogen peroxide, if a sample containing a great amount of such ingredients is measured by using an enzyme electrode with no Membrane II, an excess oxidation current response occurs, to provide a large error in the measurement for the substrate. Then, it is necessary to utilize a membrane that functions as a molecular sieve for selectively permeating only hydrogen peroxide of a relatively small molecular weight.

However, since one of at least two required membranes is an enzyme-immobilizing membrane prepared by complicated procedures, a method of manufacturing and constituting the enzyme electrode is unavoidably complicated. If an enzyme can be immobilized in a membrane that functions as a molecular sieve, only one membrane can perform the functions of the Membrane I and the Membrane II, making it possible for only one membrane to constitute the enzyme electrode. However, it is difficult to immobilize the enzyme in such a functional membrane by a simple procedure, at a high activity and stably, and no practical immobilizing method has yet been developed.

SUMMARY OF THE INVENTION

In view of the foregoing, an object of the present invention is to provide an enzyme electrode having an enzyme immobilized at a high activity and stably in a membrane that functions as a molecular sieve by a convenient procedure, which electrode exhibits excellent characteristics, such as high sensitivity, rapid response, and high durability.

Other and further objects, features, and advantages of the invention will appear more evident from the following description taken in connection with the accompanying drawing.

BRIEF DESCRIPTION OF THE DRAWINGS

FIG. 1 is a graph showing the relationship between the current response and time obtained in the electrode (Electrode I) deposited with a lactate oxidase-containing polyion complex membrane in Test Example 1 of the present invention; and FIG. 2 is a graph showing the relationship between the choline concentration and the steady current response obtained in the electrode covered with the choline oxidase-containing polyion complex membrane in Example 2 of the present invention.

DETAILED DESCRIPTION OF THE INVENTION

The present inventors, having earnestly studied the method of manufacturing an enzyme-immobilizing membrane onto an electrode, have noted that a polyion complex membrane is constituted on an electrode, when an aqueous solution of polycations and an aqueous solution of polyanions are mixed and dried on an electrode. Then we have accomplished the present invention based on the findings that an enzyme-incorporating polyion complex is formed when enzyme molecules are present in the vicinity of the polyion complex during its formation, and that the enzyme-containing polyion complex membrane is dense and exhibits a function as a molecular sieve.

That is, the present invention provides:

(1) an enzyme electrode, comprising a polyion complex membrane of an immobilized enzyme, formed on an electrode base, and (2) a method of manufacturing an enzyme electrode, comprising developing an aqueous solution of polycations (or polyanions) and an aqueous solution of an enzyme on an electrode base; then developing an aqueous solution of polyanions (or polycations), and then drying them.

There is no particular restriction on the material of the base electrode used in the present invention, and noble metals, such as platinum or gold, or carbon-type materials are used preferably in view of corrosion resistance or the like.

The polycation used in the present invention is a polymer having cationic groups, and a polymer having cationic groups in repeating units is preferably used. There can be mentioned, specifically, polylysine, poly(ethylene-imine), poly(dimethylaminoethyl methacrylate), and quaternarized poly(vinyl pyrrolidone). Further, the polyanion is a polymer having anionic groups, and a polymer having anion groups in repeating units is preferably used. There can be mentioned, specifically, poly(styrene sulfonic acid), polyglutamic acid, perfluorinated ionomer (such as Nafion; trade name, manufactured by Du Pont Co.), and poly(estersulfonic acid) (such as AQ polymer; trade name, manufactured by Eastman Kodak Co.).

There is no particular restriction on the combination of the polycation and the polyanion, and preferred combinations include the following: polylysine and poly(styrene sulfonic acid); polylysine and poly(ester-sulfonic acid); quaternarized poly(vinyl pyrrolidone) and polyglutamic acid; and polyethyleneimine and polyglutamic acid.

Referring specifically to an example of a preferred embodiment according to the present invention, after applying a pretreatment, such as polishing, to a substrate electrode, an aqueous solution of a polycation (or an aqueous solution of a polyanion) is dropped onto the surface; then an aqueous solution of an enzyme to be immobilized is next dropped, and finally an aqueous solution of a polyanion (or an aqueous solution of a polycation) is dropped. In the last dropping process, an enzyme-incorporating polyion complex becomes settled on the base electrode. When the resultant aqueous solution is air-dried, an enzyme electrode having an enzyme-immobilizing membrane disposed on the base electrode is obtained.

The ratio between the polycation and the polyanion used in this method is preferably an equivalent ratio required for forming the complex. There is no particular restriction on the concentration of the aqueous solution for the polycation and the polyanion, and it is preferred that the polycation has a concentration of 0.1 to 1% ("%" means % by weight here and hereinafter) and the polyanion has a concentration from 0.1 to 1%.

The amount of the enzyme to be immobilized differs depending on the kind of the enzyme, the activity of the enzyme electrode, or the like, and it is more than 10%, preferably 30 to 100%, based on the polyion complex. The concentration of the solution of the enzyme to be immobilized is from 0.1 to 10%, preferably about 1%.

Since the enzyme is deactivated if the aqueous solution used is extremely acidic or alkaline, it is necessary for the aqueous solution to be of a pH value that will allow the enzyme to exist stably. Suitably an aqueous solution containing the polycation, polyanion, and enzyme, which solution is dissolved, respectively, into a buffer solution at a pH value usually from 5 to 9, preferably about 7, is used.

The process for manufacturing the enzyme electrode is extremely simple, and the thickness of the enzyme-containing polyion complex membrane disposed on the electrode can also be controlled optionally. The response (response time to the addition of substrate, level of the response current, etc.) and the function as a molecular sieve of the enzyme electrode depend on the thickness of the enzyme-immobilizing membrane, and it is easy in this process to dispose a membrane of an appropriate thickness on the electrode. The thickness of the polyion complex membrane is usually more than 0.1 µm, preferably 1 to 10 µm.

A measuring system which is well known in the art can be constituted by using the thus obtained enzyme electrode as a working electrode, and combining it with an appropriate counter electrode, or a reference electrode and a counter electrode. The measuring system and measurement are described, for example, in Allen J. Bard and Larry R. Faulkner, "Electrochemical Methods—Fundamentals and Applications—," page 23, published by John Wiley & Sons (1980).

There is no particular restriction on the kind of the enzyme immobilized to the enzyme electrode according to the present invention, and lactate oxidase, alcohol oxidase, choline oxidase, and glucose oxidase are used preferably.

According to the method of the present invention, it is possible to quite easily manufacture an enzyme electrode having an enzyme-immobilizing membrane formed thereon, and the thickness can also be controlled easily.

By using the enzyme electrode of the present invention, an enzyme substrate or the like can be quantitatively determined with less hindrance of easily oxidizable coexistent materials, conveniently, exactly, and rapidly.

The enzyme electrode according to the present invention is usable in such application uses as medical instrumentation, fermentation step control, and foodstuff control.

EXAMPLE

The present invention will be explained in more detail by way of examples, to which it should be understood the present invention is not restricted.

Example 1

Preparation of an electrode deposited with a polyion complex membrane containing lactate oxidase An end face of glassy carbon of 3-mm diameter was used as a base electrode, on which was dropped 5 µl of an aqueous solution of 0.6% (w/v) polylysine hydrochloride, having an average molecular weight of 100,000 (adjusted to pH 7); then 5 µl of an aqueous 0.6% (w/v) solution of a lactate oxidase (EC No. undefined, manufactured by Sigma Co.) (pH 7) was dropped; and finally 10 µl of an aqueous 0.6% (w/v) solution of sodium poly(styrene sulfonate) having a molecular weight of 70,000 (pH 7), was dropped, and they were left and dried at room temperature for more than 2 hours, to obtain an Electrode I deposited with an enzyme-containing polyion complex membrane. The thickness of the polyion complex membrane was 5 µm. After cleaning the surface of the Electrode I sufficiently with a phosphate buffer (0.1 mol/liter, pH 7), to wash out free lactate oxidase, when the enzymatic activity on the surface was estimated by a usual method using phenol/4-aminoantipyrin/peroxidase as a color-forming system, it was 0.05 unit/cm$^2$. The value was quite comparable to the activity of the lactate oxidase-immobilizing membrane prepared by a customary usual bonding method or entrapping method.

Test Example 1

Measurement for the concentration of lactic acid by the electrode deposited with the polyion complex membrane containing lactate oxidase A three-electrode system comprising the Electrode I prepared in Example 1, as a working electrode, a silver-silver chloride electrode, as a reference electrode, and a platinum wire, as a counter electrode, was constituted and connected to a constant-voltage power source (HA-502, manufactured by Hokuto Denko Co.). The three electrodes described above were inserted in a test solution of 20-ml volume (phosphate buffer solution, pH 7.7, at 25° C.). The test solution was kept at an air-saturated state and stirred by a magnetic stirrer, and 1 V of voltage was applied to the working electrode (relative to silver-silver chloride electrode) from the constant potential power source, and the current was measured. FIG. 1 shows a graph representing the relationship between the current of the Electrode I (µA) and the time (sac) when lactic acid was added to the test solution by 0.1 mmol/liter at 0, 10, 20, and 30 sec. As is apparent from FIG. 1, the current reached a steady value 2 sec after the addition of lactic acid, and it can be seen that the concentration of lactic acid can be measured rapidly. Further, measurement for lactic acid by 0.1 mmol/liter was conducted ten times a day repeatedly every day successively, and as a result it was shown that the average value of the response current for ten times of measurements did not lower for six weeks after the preparation of the electrode and had a high durability.

Reference Example

Immobilization of lactate oxidase using photo-crosslinkable polyvinyl alcohol, and measurement of lactic acid concentration by an electrode deposited with immobilized membrane Ten mg of the above lactate oxidase was dissolved into 100 mg of an aqueous solution of photo-crosslinkable polyvinyl alcohol (10%, manufactured by Toyo Gosei Kogyo Co.), and an enzyme-immobilizing membrane (10 μm thickness) was prepared by the process of developing, drying, and photoirradiation of the solution ("Anal. Chim. Acta," Vol. 177, pages 153–166, 1985). The membrane was placed on a glassy carbon electrode of 3-mm diameter and brought into intimate contact on the surface of the electrode by using an O-ring, to prepare an Electrode II. As a result of measurement for lactic acid by using the Electrode II as the working electrode under the same conditions as those in Test Example 1, the time required for obtaining a steady current after the addition of lactic acid was 30 sec, and the durability to lactic acid measurement testing conducted ten times a day, was for three weeks.

Test Example 2

Comparison of response of the Electrodes I and II to acetaminophene, ascorbic acid, uric acid, etc For the two types of the Electrodes I and II prepared in Example 1 and the Reference Example, response current to hydrogen peroxide, acetaminophene, uric acid, ascorbic acid, and reduced nicotinamide adenine dinucleotide (NADH) (each at concentration of 0.1 mmol/liter), was recorded and compared with lactic acid response in the same manner as in Test Example 1. The results are shown in Table 1. As can be seen from Table 1, the response current to lactic acid is only less than ½ of that to hydrogen peroxide at the same concentration in Electrode I. This is considered unavoidable because, in the forming of hydrogen peroxide from lactic acid by the enzymatic reaction, although almost 100% of the hydrogen peroxide formed near the electrode of the immobilizing membrane diffuses to the electrode, the hydrogen peroxide that is formed on the side of the solution of the immobilizing membrane tends to leak to the solution. On the other hand, the response current to acetaminophene, ascorbic acid, or uric acid having a molecular weight of about one hundred and several tens, is much smaller than the response current to lactic acid at the same concentration, and NADH, of a higher molecular weight, actually gives no response current. This indicates that the enzyme-containing polyion complex membrane utilized for Electrode I functions satisfactorily as a molecular sieve. In the Electrode II prepared in the Reference Example, all of the other ingredients gave 2-fold to 5-fold larger response currents as compared with the response of lactic acid, whereas interference by easily-reducing ingredients can be suppressed in Electrode I. The concentration of acetaminophene, ascorbic acid, and uric acid in blood is usually less than ¹⁄₁₀ of the concentration of lactic acid, and accordingly from ten to several tens % of error may possibly be given to the lactic acid response in Electrode II, whereas the level of the error was reduced to less than ¹⁄₁₀ in Electrode I, and it can be seen that exact measurement is possible for the concentration of lactic acid.

TABLE 1

| Sample | Molecular weight | Electrode I | | Electrode II | |
| --- | --- | --- | --- | --- | --- |
| | | Response current (μA) | Response current ratio* | Response current (μA) | Response current ratio* |
| Hydrogen peroxide | 44 | 1.06 | 2.36 | 1.19 | 4.13 |
| Acetaminophene | 151 | 0.30 | 0.67 | 4.55 | 15.7 |
| Uric acid | 168 | 0.21 | 0.47 | 4.30 | 14.8 |
| Ascorbic acid | 171 | 0.12 | 0.27 | 4.30 | 14.8 |
| NADH | 794 | 0.01 | 0.02 | 2.40 | 8.27 |
| Lactic acid | 90 | 0.45 | 1 | 0.29 | 1 |

(note)
*: Ratio relative to lactic acid response assumed as 1.

Example 2

Preparation of an electrode coated with choline oxidase-containing polyion complex membrane, and choline response of the electrode An end face of glassy carbon of 3-mm diameter was used as a base electrode, on which were dropped 5 μl of an aqueous solution of 0.6% (w/v) of polylysine hydrochloride, having an average molecular weight of 100,000 (adjusted to pH 7), 5 μl of an aqueous 0.6% (w/v) solution of choline oxidase (EC 1.3.17, manufactured by Toyobo Co.) (pH 7), and, finally, 10 μl of an aqueous 0.6% (w/v) solution of sodium poly(styrene sulfonate), having a molecular weight of 70,000 (pH 7), and they were left and dried at room temperature for more than 2 hours, to obtain an electrode deposited with an enzyme-containing polyion complex membrane. After cleaning the surface of the electrode sufficiently with a phosphate buffer (0.1 mol/liter, pH 7), to wash out free choline oxidase, when the enzymatic activity on the surface was estimated by a usual method using phenol/4-aminoantipyrine/peroxidase as a color-forming system, it was 0.02 unit/cm². The value was quite comparable to the activity of the lactate oxidase-immobilizing membrane prepared by a usual chemical bonding method or entrapping method.

When the choline response was evaluated under the same conditions as those in Test Example 1, a steady current was obtained five sec after the addition of choline. FIG. 2 shows a graph representing the relationship between the steady current and the choline concentration. As is apparent from FIG. 2, a linear relationship was obtained between both of them within a range from 0.5 μmol/liter to 0.2 mmol/liter, and choline can be measured within this range of concentration.

Having described our invention as related to the present embodiments, it is our intention that the invention not be limited by any of the details of the description, unless otherwise specified, but rather be construed broadly within its spirit and scope as set out in the accompanying claims.

What we claim is:

1. An enzyme electrode, comprising a polyion complex membrane of an immobilized enzyme, formed on an electrode base, wherein the polyion complex membrane comprises at least one polycation and at least one polyanion, and wherein said at least one polycation is selected from the group consisting of polylysine, poly(ethyleneimine), poly (dimethylaminoethyl methacrylate), and quaternarized poly (vinyl pyrrolidone).

2. The enzyme electrode as claimed in claim 1, wherein the polyanion is selected from the group consisting of poly(styrene sulfonic acid), polyglutamic acid, perfluorinated ionomer, and poly(ester-sulfonic acid).

3. A method of manufacturing an enzyme electrode, comprising
(i) applying an aqueous solution of at least one polycation or at least one polyanion and an aqueous solution of an enzyme on an electrode base to form a first mixture of said at least one polycation or at least one polyanion and said enzyme;
(ii) applying an aqueous solution of at least one polyanion or at least one polycation on said first mixture to form a second mixture, wherein when step (i) applies at least one polycation, step (ii) applies at least one polyanion and when step (i) applies at least one polyanion, step (ii) applies at least one polycation; and
(iii) drying said mixtures of aqueous solutions of at least one polycation, at least one polyanion, and enzyme.

4. The method as claimed in claim 3, wherein step (i) comprises sequentially applying
(a) the aqueous solution of at least one polycation or at least one polyanion, and
(b) the aqueous solution of an enzyme on the aqueous solution of (a) on the base electrode.

5. The method as claimed in claim 3, wherein the polycations are polymers having cationic groups.

6. The method as claimed in claim 3, wherein said at least one polycation is selected from the group consisting of polylysine, poly(ethyleneimine), polydimethylaminoethyl methacrylate), and quaternarized poly(vinyl pyrrolidone).

7. The method as claimed in claim 3, wherein the polyanions are polymers having anionic groups.

8. The method as claimed in claim 3, wherein said at least one polyanion is selected from the group consisting of poly(styrene sulfonic acid), polyglutamic acid, perfluorinated ionomer, and poly(ester-sulfonic acid).

* * * * *